(12) United States Patent
Anuzis et al.

(10) Patent No.: US 6,928,370 B2
(45) Date of Patent: Aug. 9, 2005

(54) HEALTH MONITORING

(75) Inventors: Paul Anuzis, Derby (GB); Steve P. King, Derbyshire (GB); Dennis M. King, Derby (GB); Lionel Tarassenko, Oxford (GB); Paul Hayton, Oxfordshire (GB); Simukai Utete, Oxford (GB)

(73) Assignee: Oxford Biosignals Limited, Oxford (GB)

(*) Notice: Subject to any disclaimer, the term of this patent is extended or adjusted under 35 U.S.C. 154(b) by 219 days.

(21) Appl. No.: 09/898,008

(22) Filed: Jul. 5, 2001

(65) Prior Publication Data

US 2002/0040278 A1 Apr. 4, 2002

(30) Foreign Application Priority Data

Jul. 5, 2000 (GB) .............................. 0016561

(51) Int. Cl.⁷ .............................. G06F 19/00
(52) U.S. Cl. .......................... 702/56; 702/35
(58) Field of Search .............. 702/56, 34, 35; 340/683; 703/2, 8

(56) References Cited

U.S. PATENT DOCUMENTS

| | | | | |
|---|---|---|---|---|
| 5,206,816 A | * | 4/1993 | Hill et al. ................ | 702/56 |
| 5,210,704 A | * | 5/1993 | Husseiny ................ | 702/34 |
| 5,402,521 A | | 3/1995 | Niida et al. | |
| 5,684,718 A | | 11/1997 | Jenkins et al. | |
| 5,774,376 A | * | 6/1998 | Manning ................ | 702/56 |
| 5,784,273 A | * | 7/1998 | Madhavan ............... | 700/71 |
| 5,847,658 A | * | 12/1998 | Irie et al. ............... | 340/683 |
| 5,995,910 A | * | 11/1999 | Discenzo ................ | 702/56 |

FOREIGN PATENT DOCUMENTS

| | | |
|---|---|---|
| EP | 0 908 805 A1 | 4/1999 |
| EP | 1 014 054 A2 | 6/2000 |
| GB | 2 135 061 A | 8/1984 |
| GB | 2 256 491 A | 12/1992 |
| GB | 2 277 151 A | 10/1994 |
| GB | 2 349 952 A | 11/2000 |

OTHER PUBLICATIONS

Patel et al., Gas Turbine Engine Condition Monitoring Using Statistical and Neural Network Methods, 1996, The Institution of Electrical Engineers, IEE.*

Greitzer et al., Gas Turbine Engine Health Monitoring and Prognostics, Aug. 30–Sep. 2, 1999, International Society of Logistics (SOLE) Symposium.*

Caulkins et al., Applying Neural Networks to Determine Vibration Parameters in a Turbine, 1999 IEEE.*

(Continued)

*Primary Examiner*—John Barlow
*Assistant Examiner*—Toan M. Le
(74) *Attorney, Agent, or Firm*—Oliff & Berridge, PLC

(57) ABSTRACT

A method for monitoring the health of a system comprises performing at each of a plurality of times the steps of:

constructing a condition signature from a plurality of condition indicators including (a) a plurality of vibration measurements acquired from the system or (b) one or more vibration measurements and one or more performance parameter measurements acquired from the system;

predicting a normal signature from a model defining one or more inter-dependencies between said condition indicators, the normal signature corresponding to the condition signature for a healthy system;

comparing the condition signature with the normal signature; and registering an event if the condition signature differs from the normal signature by more than a predetermined threshold.

19 Claims, 9 Drawing Sheets

OTHER PUBLICATIONS

DePold et al., The Application of Expert Systems and Neural Networks to Gas Turbine Prognostics and Diagnostics, Oct. 1999, Journal of Engineering for Gas Turbines and Power, vol. 121, pp. 607–612.*

"Application of a Neural Network in Gas Turbine Control Sensor Fault Detection", Simani et al., Proceeding of the 1998 IEEE International Conference on Control Applications, Trieste, Italy, Sep. 1–4, 1998.*

Gelb et al., " Applied Optimal Estimation", MIT Press 1974, pp. 102–155.

Nairac et al., "A System for the Analysis of Jet Engine Vibration Data", *Integrated Computer–Aided Engineering*, vol. 6, No. 1, pp. 53–65, 1999.

Ghahramani et al., "Parameter Estimation for Linear Dynamical Systems", Technical Report CRG–TR–96–2, University of Toronto, Feb. 22, 1996, pp. 1–6.

Roweis et al., "A Unifying Review of Linear Gaussian Models", Neural Computation, vol. 11, 1999, pp. 305–345.

Ghahramani et al., "Learning Nonlinear Dynamical Systems using an EM Algorithm", in Kearns et al. (ed), *Advances in Neural Information Processing Systems*, vol. 11, MIT Press, 1999.

X, Li et al. "Fault prognosis for large rotating machinery using neural network" Application of artificial intelligence in engineering IX. Proceedings of the ninth international conference, proceedings of ninth international conference on applications of artificial intelligence in engineering. Aieng 94, Malvern, PA, USA 19–21 J, pp. 99–105.

* cited by examiner

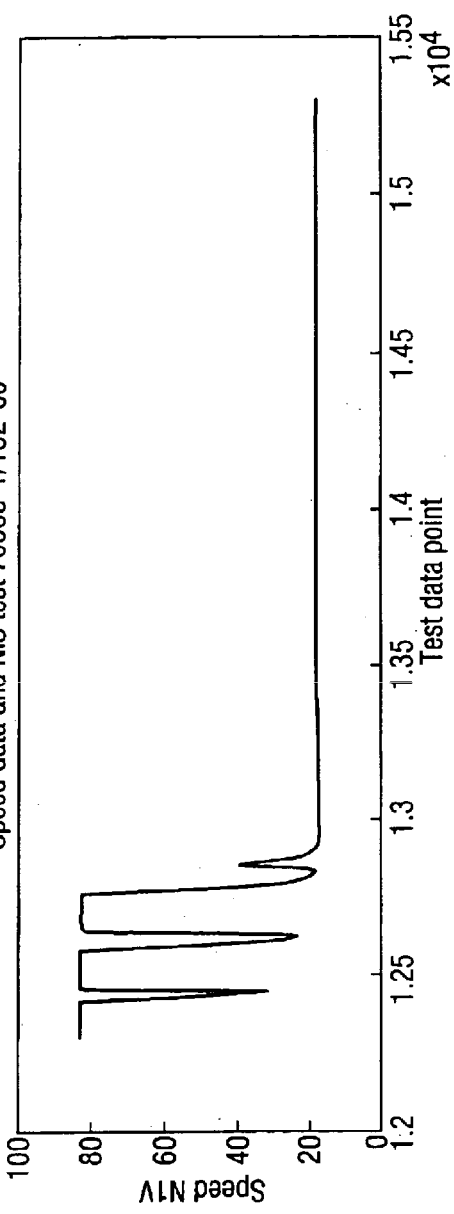
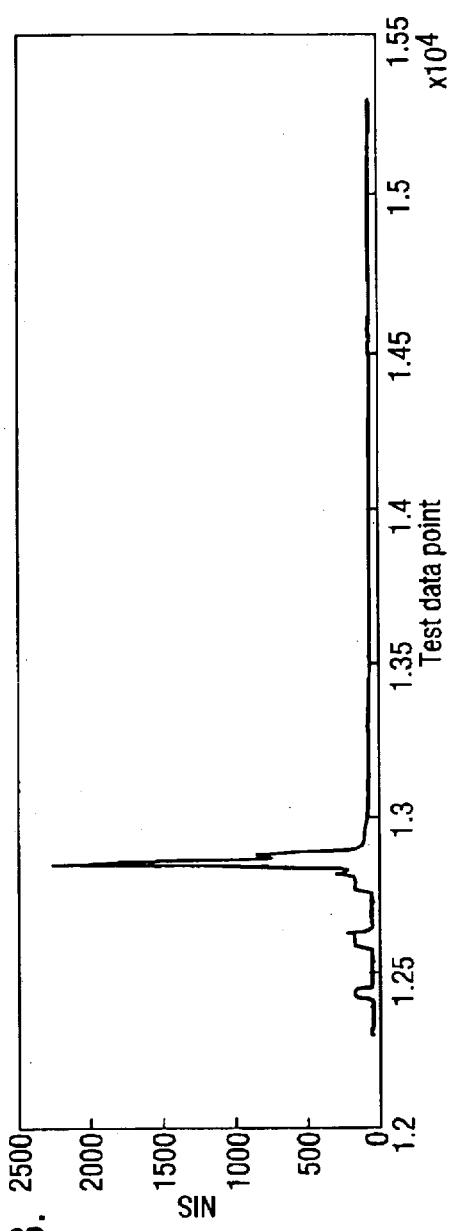
Fig. 7.
Fig. 8.

HEALTH MONITORING

FIELD OF THE INVENTION

This invention relates to methods and data processing systems for monitoring the health of a system. The methods and data processing systems of the invention are particularly, although not necessarily exclusively, suitable for monitoring the health of power plant, including for example gas turbine, spark ignition and compression ignition internal combustion engines.

BACKGROUND

The health of a system can be considered a measure of the condition of a system against expected norms. A healthy system is one whose condition closely matches expectations, whereas an unhealthy system is one whose condition differs from what would be expected, indicating for example deterioration of, or a possible problem with the system. The ability to monitor the health of a system can therefore allow such deterioration and/or problems to be detected and, if necessary, addressed at an early stage.

For example, U.S. Pat. No. 5,684,718 describes a non-real time system for monitoring the operation of an electric generator in which vibration and load data are combined to produce a single signal which is then compared with stored data representative of maximum acceptable combinations of the two parameters. Essentially the system is an automated "look up table" which issues warnings when vibrations have exceeded acceptable limits.

In order to determine the condition, and consequently health, of a system, it is normal to monitor and analyse a series of measurable indicators which themselves reflect aspects of the condition of the system. For instance, taking the example of a gas turbine, one might monitor performance parameters such as turbine and compressor operating temperatures and pressures and spool speeds. To obtain a fuller overall picture of the engine's condition, these performance parameters can be supplemented with further condition indicators including, for example, vibration measurements and measurements of the particulate material entrained in the circulating oil.

Particularly with complex mechanical Systems such as gas turbines, the number of indicators that must be monitored to obtain a useful overall picture of the system's condition can be high. This in turn means that the task of analysing the complete series of indicators to determine the health of the engine is a complex one, typically requiring a skilled expert to analyse the data off-line.

Taking again the example of a gas turbine, it is known for example to collect performance and vibration data from the engine over time to be analysed off-line by one or more experts. Typically the performance data will be compared with simulated data for the same engine and, based on this comparison, an expert will form a view as to the health of the engine. Additionally, a small amount of vibration data will be reviewed, giving a superficial view of gross changes in engine behaviour. If a problem is detected, the vibration data may then be analysed in more detail, often by another expert, to look for any abnormal indications which might be symptomatic of underlying mechanical problems which could lead to a loss of health and operability.

SUMMARY OF THE INVENTION

It is a general aim of the present invention to provide methods and data processing systems that facilitate the acquisition and analysis of condition indicators in a manner such that the overall health of a system can be more readily assessed.

Accordingly, in general terms a first aspect of the invention provides a method for monitoring the health of a system, comprising:

constructing a condition signature from a plurality of measured condition indicators acquired from the system;

comparing the condition signature with a normal signature, corresponding to the signature for a healthy system; and registering an event if the condition signature differs from the normal signature by more than a predetermined threshold.

The term "signature", as used herein, pertains to the values of a plurality of condition indicators merged or fused into a unit or quantity such as a set, vector or scalar. In the example of a vector signature, the indicators may correspond to respective elements of the vector. In the example of a scalar signature, the magnitude of the scalar may be determined by a mathematical function which acts upon the indicator values.

By merging or fusing the condition indicators into a single signature in this manner, and providing a normal signature with which the fused data can be compared, the task of assessing the health of a system is greatly simplified. In particular, since the detection of an event amounts to an indication of a potential problem or an unhealthy system (i.e. a system condition that differs from what would normally be expected), the monitoring of the health can be largely automated, removing, or at least minimising, the requirement for expert input during the monitoring process. This in turn means that it becomes feasible to continuously monitor the health of a system, and to provide useful information about the health of the system in real time during operation.

Preferably the condition indicators that are combined to form the system condition signature include operational parameters, which in the case of a mechanical system may be speeds, pressures (e.g. gas pressures, oil pressures) and temperatures for example. Other useful parameters may include what might be conventionally thought of as control or status parameters. For convenience, such parameters will be referred to using the single label of "performance parameters" in the following text.

Additionally, to obtain a fuller picture of a mechanical system's health, it is particularly preferred that the signature includes one or more condition indicators related to the vibration of the system.

Put, more generally, the condition indicators from which the system condition signature is constructed may be derived from two or more disparate sources of data. This illustrates a particular strength of this approach in that a great variety of different forms of condition indicator data can be encompassed in the system condition signature, providing a more comprehensive measure of the system's health than has previously been possible without multiple analyses.

Preferably at least three condition indicators are used to construct the condition signature. More preferably at least 10 and even more preferably at least 20 condition indicators are used to construct the condition signature.

In a preferred embodiment, the system comprises a gas turbine engine.

The normal signature for the system can be derived from a predefined model of the system that is being monitored. This model can itself be developed off-line and then fixed for the duration of the operation of the health monitoring method. More preferably, however, the model is designed to be refined as the method proceeds in order that it might be better tuned to a specific system.

Whichever approach is adopted, it is particularly preferred that the model is a "learnt model" developed using a data-driven, or at least partially data-driven approach. That is to say the learnt model learns from training data comprising series of the condition indicators which have been labelled as normal (i.e. healthy) or abnormal (i.e. unhealthy) as the case may be. In fact, it is often the case that normal data is far more readily available than abnormal data and therefore the training data may only include examples of normal data. This still results in an effective model, because subsequent events can then be identified as departures from the learnt model of normality.

The normal signature for the healthy system may be predicted from a model defining one or more inter-dependencies between the condition indicators. This enables the model to specify a continuous boundary in N-dimensional space (where each dimension relates to one of N condition indicators) corresponding to the limits of healthy system operation. This is in contrast to "look up table" approaches for setting the limits of healthy system operation which do not capture the (often complex) inter-relationships and correlations between condition indicators.

So, for example, it is often the case that the onset of a problem or failure in a particular system manifests itself in small changes to a number of condition indicators which individually, however, remain in their respective allowable ranges. The "look up table" approach, which is only able to sense gross shifts in individual parameters, would fail to recognise that a problem or failure had occurred. In contrast, when the condition signature for the healthy system is predicted from a model defining one or more inter-dependencies between the condition indicators the several small changes in the condition indicators may have the cumulative effect of driving the condition signature outside normal boundary in N-dimensional space.

Preferably, the predetermined threshold corresponds to a statistically significant departure or variance from normality as defined by the normal signature. Thus, in the example of a normal signature provided by a learnt model, further development of the model (e.g. due to the input of more training data) will result in a corresponding variation in the predetermined threshold.

In one embodiment, the invention provides a method for monitoring the health of a system, which comprises performing at each of a plurality of times the steps of:

constructing a condition signature from a plurality of condition indicators including (a) a plurality of vibration measurements acquired from the system or (b) one or more vibration measurements and one or more performance parameter measurements acquired from the system;

predicting a normal signature from a model defining one or more inter-dependencies between said condition indicators, the normal signature corresponding to the condition signature for a healthy system;

comparing the condition signature with the normal signature; and registering an event if the condition signature differs from the normal signature by more than a predetermined threshold.

The model may comprise a matrix (e.g. a covariance matrix) with one or more non-zero off-diagonal terms to define the inter-dependencies. The step of comparing the condition signature with the normal signature may then involve calculating a value for the normalised innovations squared (NIS) which is defined below in the "Description of the Embodiments".

Alternatively, the model may comprise a neural network. If there are N condition indicators, one embodiment is a neural network which is trained to predict the value of the $N^{th}$ from the other N−1 indicators. The step of comparing the condition signature with the normal signature may then involve calculating a prediction error which is e.g. the square of the difference between the predicted value for N and the actual value. There may be N of these predictive networks operating in parallel for each of the condition indicators. In this case the total prediction error can be the sum of the prediction errors of each of the networks. In another embodiment, a neural network is trained to predict a subset of N1 condition indicators (such as vibration values, e.g. at a number of key frequencies) from another subset of N2 condition indicators (such as the performance parameters), where N1+N2=N.

Preferably the times define successive intervals of at most 1 sec duration (i.e. a 1 Hz repetition frequency). More preferably the times define successive intervals of at most 0.2 sec duration (a 5 Hz repetition frequency), even more preferably at most 0.1 sec (a 10 Hz repetition frequency). By acquiring and processing the condition indicator data at such rates, it is possible for the method to monitor the health of the system in real time. Therefore, if an abnormal event is registered at any time, immediate and appropriate action can be taken by the system operator. This can be particularly advantageous for the operation of safety critical plant such as aero gas turbine engines.

The data acquisition rate can, however, be significantly faster than the processing rate. For example the data acquisition rate may be in the range 20 Hz to 80 kHz. Only a subset of the acquired data may then be processed.

Thus in another embodiment, the invention provides a method for monitoring the health of a system, which comprises performing at each of a plurality of times defining successive intervals of at most 1 sec duration the steps of:

constructing a condition signature from a plurality of condition indicators including (a) a plurality of vibration measurements acquired from the system or (b) one or more vibration measurements and one or more performance parameter measurements acquired from the system;

predicting a normal signature corresponding to the condition signature for a healthy system:

comparing the condition signature with the normal signature: and registering an event if the condition signature differs from the normal signature by more than a predetermined threshold.

Where the condition signature is comprised of data from disparate sources, for instance performance and vibration data, a problem occurs in that the data may well not be synchronised in time. If this asynchronous data is combined to form the signature, a distorted picture of the system's health may well result. For similar reasons, training data used to develop a model of normal system behaviour should also be synchronised if distortions in the model are to be avoided.

Thus preferably, the condition indicators are synchronously acquired from the system to a synchronisation imprecision of at most 1 sec. More preferably the synchronisation imprecision is at most 0.1, 0.075, 0.0625 or 0.02 sec. By "synchronisation imprecision" we mean the maximum difference between the acquisition times of each pair of condition indicators forming a particular condition signature. Desirably, the measurements are acquired from the system at a synchronisation imprecision which is less than the duration of the successive time intervals, e.g. if the time intervals are of 0.2 sec duration, the synchronisation imprecision may be at most 0.075 sec.

The invention also provides a data processing system for monitoring the health of a system suitable for performing the method outlined above. In general terms the data processing system comprises:

data acquisition means for acquiring a plurality of measured condition indicators from the system;

processor means for constructing a system condition signature from said plurality of measured condition indicators;

comparator means for comparing the system condition signature with a predefined normal signature, corresponding to the signature for a healthy system; and means for registering an event if the comparator indicates that the system condition signature differs from the normal signature by more than a predetermined threshold.

The data processing system may further comprise a display means for displaying (a) one or more of the condition indicators, (b) the result of the comparison of the system condition signature with the-normal signature and/or (c) an alert signal when the comparator indicates that the predetermined threshold has been transgressed (i.e. an event has been registered).

In one embodiment, the invention provides a data processing system for monitoring the health of a system, comprising:

data acquisition means for acquiring a plurality of condition indicators from the system at each of a plurality of times, the condition indicators including (a) a plurality of vibration measurements or (b) one or more vibration measurements and one or more performance parameter measurements;

processor means for constructing a condition signature from said condition indicators and for predicting a normal signature corresponding to the condition signature for a healthy system, the normal signature being predicted by a model which defines one or more inter-dependencies between said condition indicators;

comparator means for comparing the condition signature with the normal signature; and registration means for registering an event if the comparator indicates that the condition signature differs from the normal signature by more than a predetermined threshold.

In another embodiment, the invention provides a data processing system for monitoring the health of a system, comprising:

data acquisition means for acquiring a plurality of condition indicators from the system at each of a plurality of times defining successive intervals of at most 1 sec duration, the condition indicators including (a) a plurality of vibration measurements or (b) one or more vibration measurements and one or more performance parameter measurements;

processor means for constructing a condition signature from said condition indicators and for predicting a normal signature corresponding to the condition signature for a healthy system;

comparator means for comparing the condition signature with the normal signature; and registration means for registering an event if the comparator indicates that the condition signature differs from the normal signature by more than a predetermined threshold.

A further aspect of the invention addresses the problem of the synchronous acquisition of the condition indicators. The invention proposes to associate time stamps (based on a common clock) with the acquired date and to synchronise the data on the basis of these time stamps.

Accordingly, in this aspect, the invention provides a method of synchronising two or more data streams, each data stream comprising a series of sequentially acquired data elements (and relating e.g. to a respective condition indicator of the previous aspect), the method comprising:

associating a time stamp with each data element of each stream, the time stamp identifying the time of acquisition of the data element on the basis of a clock common to all data streams;

selecting a first data element from a first stream and inspecting its time stamp;

conducting a search of the data elements of the or each other stream to identify the data element in the or each other element having an associated time stamp closest to that of the selected element of the first stream; and marking said identified data element of the or each other stream and said selected element of the first stream as being synchronised with one another.

Because, the relative acquisition times of the data elements are generally more significant than their absolute acquisition times, the common clock may be operate within an absolute or relative framework. In an absolute framework one clock provides the time stamp for each data element of each data stream. In a relative framework each data stream has its own clock, and one of the clocks is selected as the reference clock against which the acquisition times of the other data streams are measured. It may be convenient to use a mixture of absolute and relative frameworks. For example, if the data streams relates to performance parameter and vibration measurements, the performance parameter measurements may be time stamped from one clock and the vibration measurements from another clock.

The process can be repeated until the data elements in the first stream have been exhausted. In any subsequent processing of the data that is reliant on using synchronised data streams, only those data elements marked as being synchronised with one another are used.

In the case where the acquisition rates of the data streams differ from one another, it is preferred that the first stream, with which the other streams are synchronised, is chosen to be the stream having the lowest acquisition rate.

The invention further provides a data processing system for synchronising two or more data streams, each data stream comprising a series of sequentially acquired data elements, comprising:

means for associating a time stamp with each data element of each stream, the time stamp identifying the time of acquisition of the data element on the basis of a clock common to all data streams;

means for selecting a first data element from a first stream and inspecting its time stamp;

means for conducting a search of the data elements of the or each other stream to identify the data element in the or each other element having an associated time stamp closest to that of the selected element of the first stream; and means for marking said identified data element of the or each other stream and said selected element of the first stream as being synchronised with one another.

BRIEF DESCRIPTION OF THE DRAWINGS

The various aspects of the invention will be further described by way of example with reference to the accompanying drawings, in which:

FIG. 7 shows the measured low pressure shaft speed (N1V) for the period of the test data from a more elaborate example of the system model, FIG. 8 shows the value for the NIS over the same period as FIG. 7.

DESCRIPTION OF THE EMBODIMENTS

Figure 1:
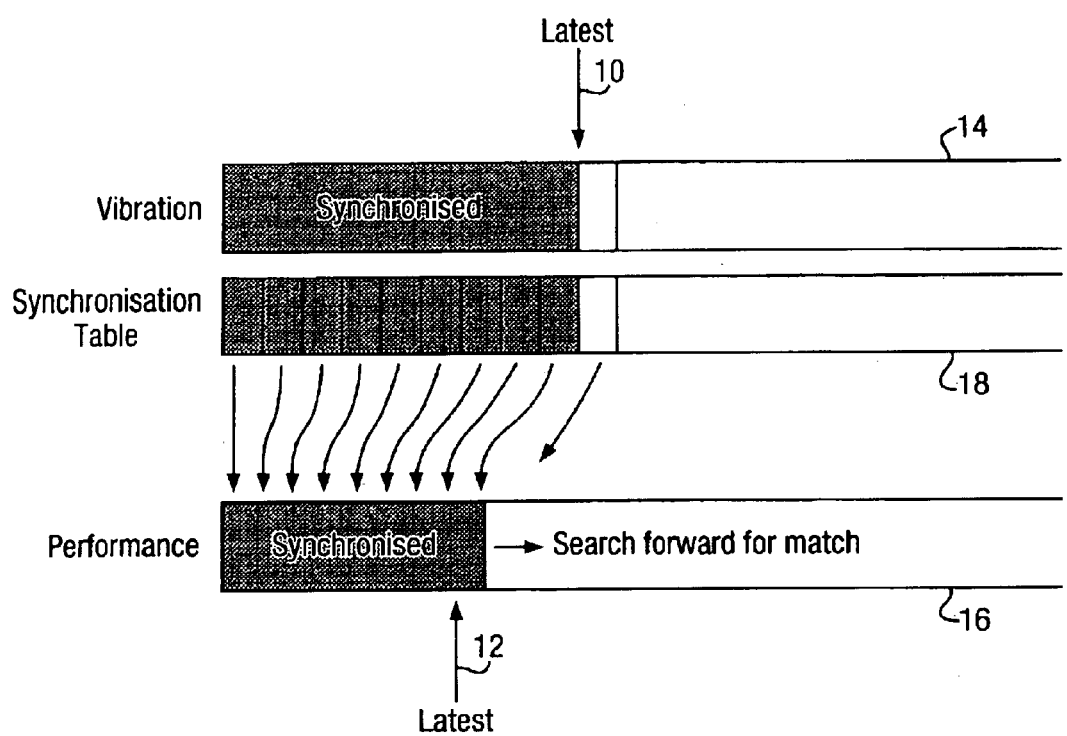
FIG. 1 schematically illustrates an exemplary data structure that can be adopted for operation of the second aspect of the invention.

The embodiment described below is an example of a data processing system employing both aspects of the invention discussed above. More specifically, it is a system for synchronous acquisition, analysis and display of performance parameters and vibration data from a power plant (e.g. a gas turbine), for monitoring the health of the plant.

In accordance with a preferred form of the second aspect, the performance and vibration data streams are synchronized in real time and, in accordance with a preferred aspect of the first aspect of the invention, these data are combined or fused to construct a signature for the system that can be compared to a signature derived from a model representing a healthy power plant, in order to provide anomaly/event detection and hence fault diagnosis.

The following discussion focusses on an application of the system to monitoring the health of a gas turbine aero-engine, but it will be appreciated that the methods can be adapted to other power plant, including for example ground-based and marine gas turbines, and spark ignition and compression ignition internal combustion engines, as well as other mechanical, thermodynamic, fluid, electrical or electronic systems. The system acquires performance parameters from the gas turbine digitally via an ethernet link at a rate between 20 and 40 Hz. Typical performance parameters are measurements of pressure, temperature, thrust, altitude or Mach number. Vibration data is acquired from analogue vibration transducers which are sampled at user-selectable sampling rates (from 625 Hz to 80 kHz) via an analogue-to-digital converter. The amplitude spectrum of the vibration data is generated using the Fast Fourier Transform every 0.2 sec.

The performance and vibration data streams are asynchronous and stored in separate files together with the corresponding timestamps. During review, as data is loaded into memory, synchronisation is performed between the performance and spectrum data on a line by line basis. Markers 10,12 (see FIG. 1) are kept which record the last synchronised line in the vibration and performance data ring buffers 14,16. When new data is available in memory, the timestamp tar the next vibration spectrum line is examined. The synchronisation algorithm starts from the last previously synchronised location in the performance data and searches forwards or backwards based on the timestamps of the performance data (accurate to 0.05 sec) until the closest matching timestamp in the performance data ring buffer 16 is identified. This location in the performance data is recorded as being synchronised with the line in the vibration ring buffer 14. The algorithm then proceeds to the next line in the vibration ring buffer 14 (0.2 sec later) and so on until there is no more data available to synchronise.

Clearly, therefore, if the performance parameters are acquired at 20 Hz (i.e. at 0.05 sec intervals) the synchronisation precision is 0.075 sec (i.e. half the acquisition interval added to the accuracy of the timestamps) and if the performance parameters are acquired at 40 Hz (i.e. at 0.025 sec intervals) the synchronisation precision is 0.0625 sec.

Considering the synchronisation algorithm in a little more detail, it can be seen from FIG. 1 that the algorithm maintains a synchronisation table 18 that gives the index of the performance data entry that matches each vibration data line. The algorithm uses variables to mark the latest synchronised data in each buffer. The operation of the algorithm can be summarised by the following 'pseudo code':

1. Initialise the latest synchronised markers to the start of the vibration and performance data.
2. Loop while there is more data in both ring buffers.
    (a) Starting from the latest synchronised data item in each ring buffer, examine the time stamp, t, on the next entry in the vibration ring buffer.
    (b) Search forward in the performance ring buffer until a time stamp greater than t is found. Select between this entry in the performance ring buffer and the previous entry for one which is closest to t and record the match in the synchronisation table.

Once synchronised, the analysis of this performance and vibration data relies on constructing models of normal jet engine behaviour and then detecting an event or an abnormality with respect to these models.

Traditional aircraft engine monitoring systems are based on two distinct processors: the use of vibration signatures to indicate engine state, and a separate procedure, gas-path analysis, which is employed for determination of state from performance parameters. In the approach described now, however, performance-related parameters such as pressure and temperature can be fused with vibration data (such as tracked order vectors—the narrow range centered on the main vibration frequencies for each shaft of the turbine). The aim is to take advantage of disparate sources of data to form a more comprehensive picture of engine state during normal operation. This in turn should allow a wider range of deviations to be identified.

Furthermore, it is proposed to employ learnt data-driven models to model a normal engine. Thus, although models of the engine system are used, these are not fixed. Instead, they evolve with acquired training data. This offers the important advantage of robustness.

The methods of data analysis described below may be termed "novelty detection". An advantage of the methods is that the role of the expert need only be retained in classifying training data as abnormal (i.e. novel) or normal. The use of Kalman filtering systems in novelty detection has been described in e.g. M. Gelb, *Applied Optimal Estimation*. MIT Press 1974.

Two alternative data analysis methods are described below. They are distinguished by the amount of prior knowledge required to set up the system. In both cases, the role of the expert need only be retained in classifying training data as novel or normal.

The first method relies on a prior learnt model of normality. For example, normal vibration tracked order shapes are learnt using a simple clustering model for the normal data. The novelty of e.g. the vibration signature for an engine under test is assessed by comparing the closeness of its tracked order signature with the prototypical patterns in the clustering model of normality. This can be done, for example, by computing the shortest normalised Euclidean distance between the vector encoding the tracked order shaped to any of the (prototypical patterns) cluster centers in the model of normality (see Nairac et al, "A System for the Analysis of Jet Engine Vibration Data", *Integrated Computer-Aided Engineering*, 6(1):53–65, 1999). If this distance is beyond a previously set threshold, the vibration signature as represented by that tracked order is deemed to be outside the bounds of normality. In addition to the vibration tracked orders, the model of normality for the vibration spectra includes the following: sidebands, multiple harmonics, fractional harmonics and broadband power.

Figure 2:
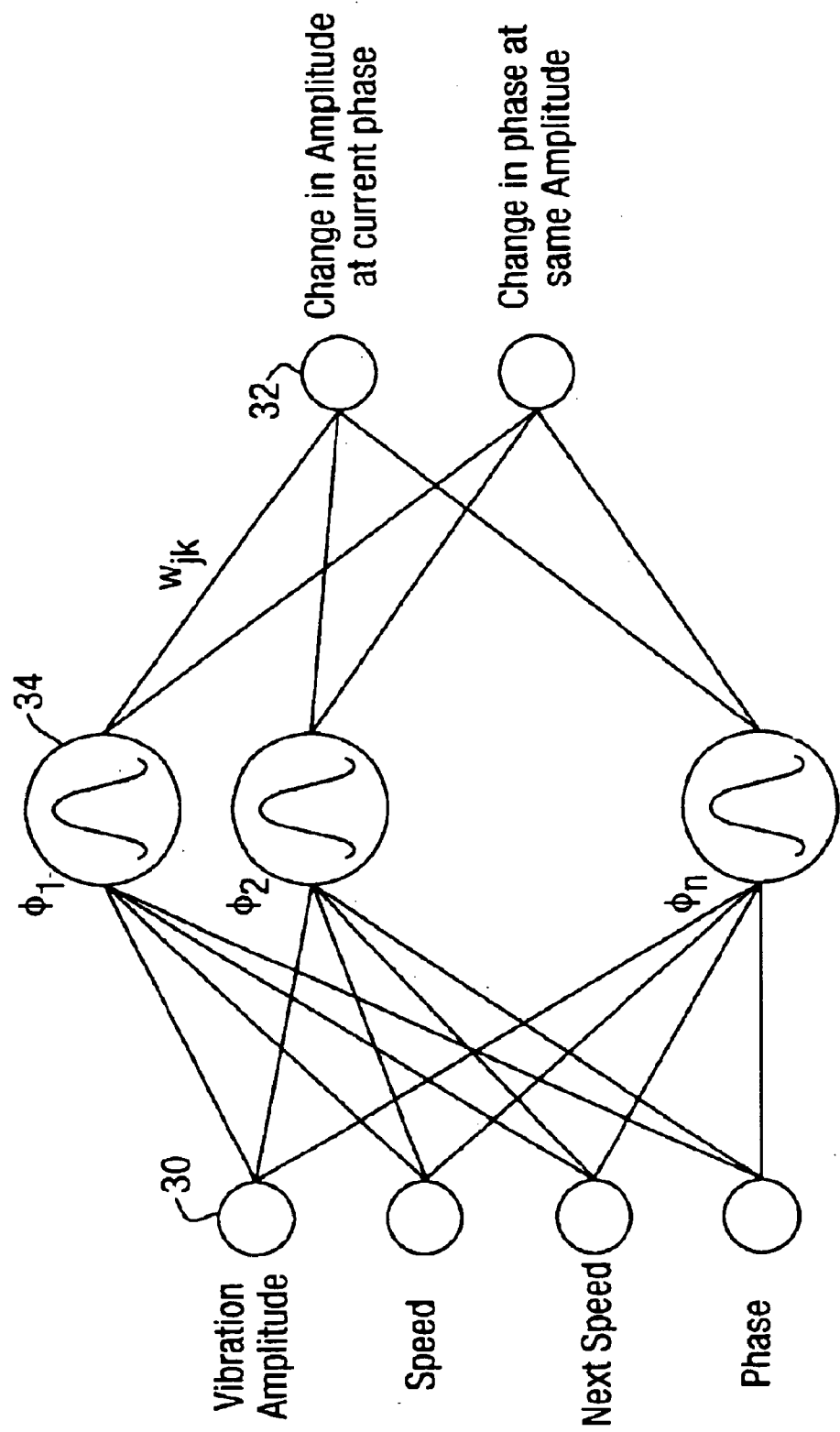
FIG. 2 shows a neural network architecture for a learnt model for operation of the first aspect of the invention.

The model is illustrated by an example in which a neural network having the architecture shown in FIG. 2 was developed as the learnt model.

The neural network had an input layer 30 with four nodes for a condition signature consisting of four condition indicators measured relating to one shaft of a multi-shaft test engine. The condition indicators were the vibration amplitude, the phase and the shaft speed all at a specified time, and the shaft speed a time increment after the specified time.

The output layer 32 of the network had two nodes for predicting respectively the change in vibration amplitude and change in phase after the time increment.

The network had one hidden layer 34, each node of which contained a Gaussian radial basis function.

The training phase for network used training data obtained from the test engine over a range of normal operating conditions. The centers and the spreads of the Gaussians were fixed using the cluster analysis described above and the weights of the connections between the nodes were then iteratively adjusted until the model converged.

Figure 3:
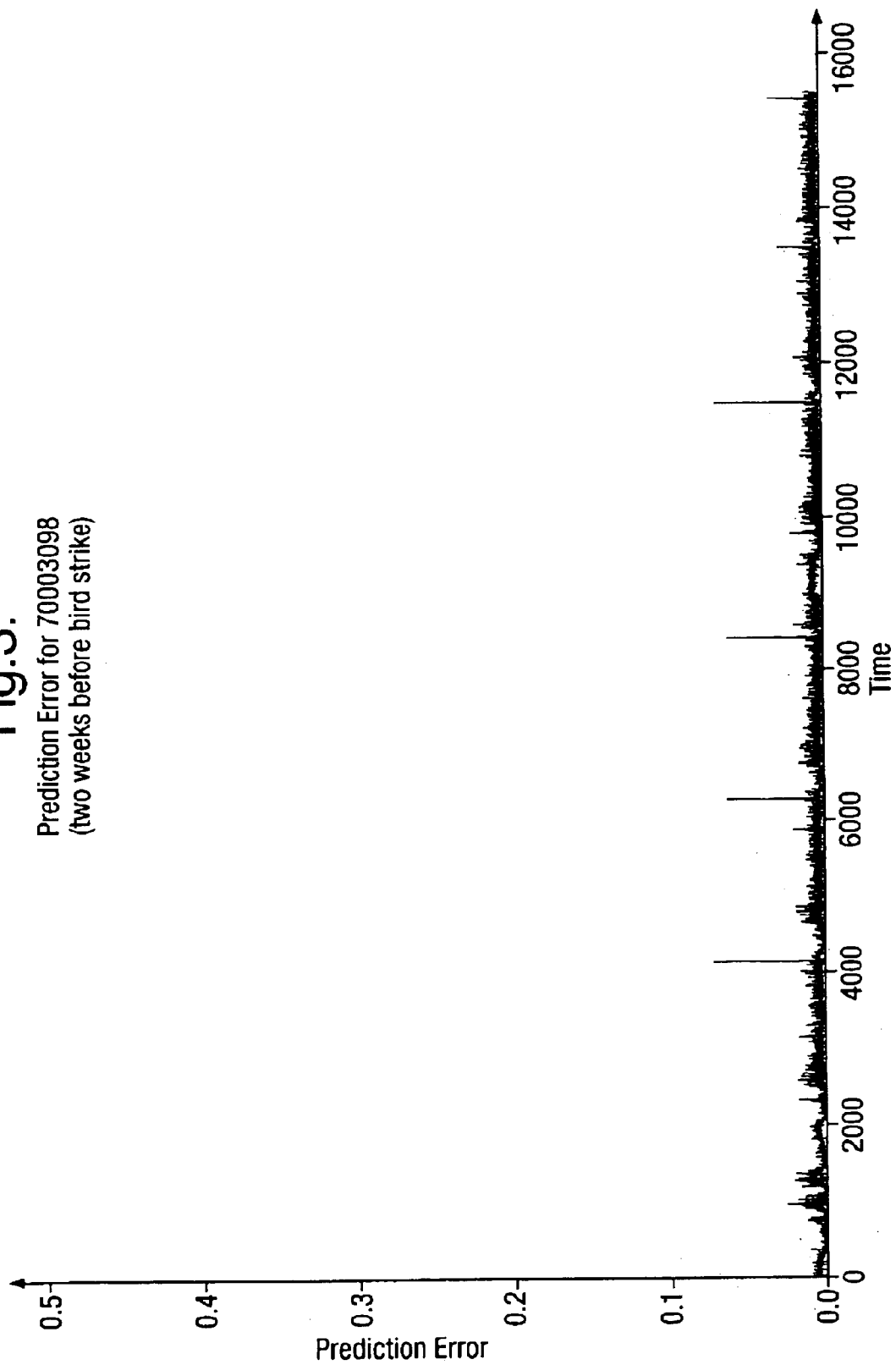
FIG. 3 shows a graph of the prediction error for the learnt model on a set of test data corresponding to a period of normal operating conditions for an engine.

FIG. 3 shows a graph of the prediction error (i.e. the sum of the prediction errors of the change in vibration amplitude and change in phase) for the model on a set of test data which also corresponded to a period of normal operating conditions for the engine. This graph provides a baseline of prediction error variation against which novel events can be judged.

Figure 4:
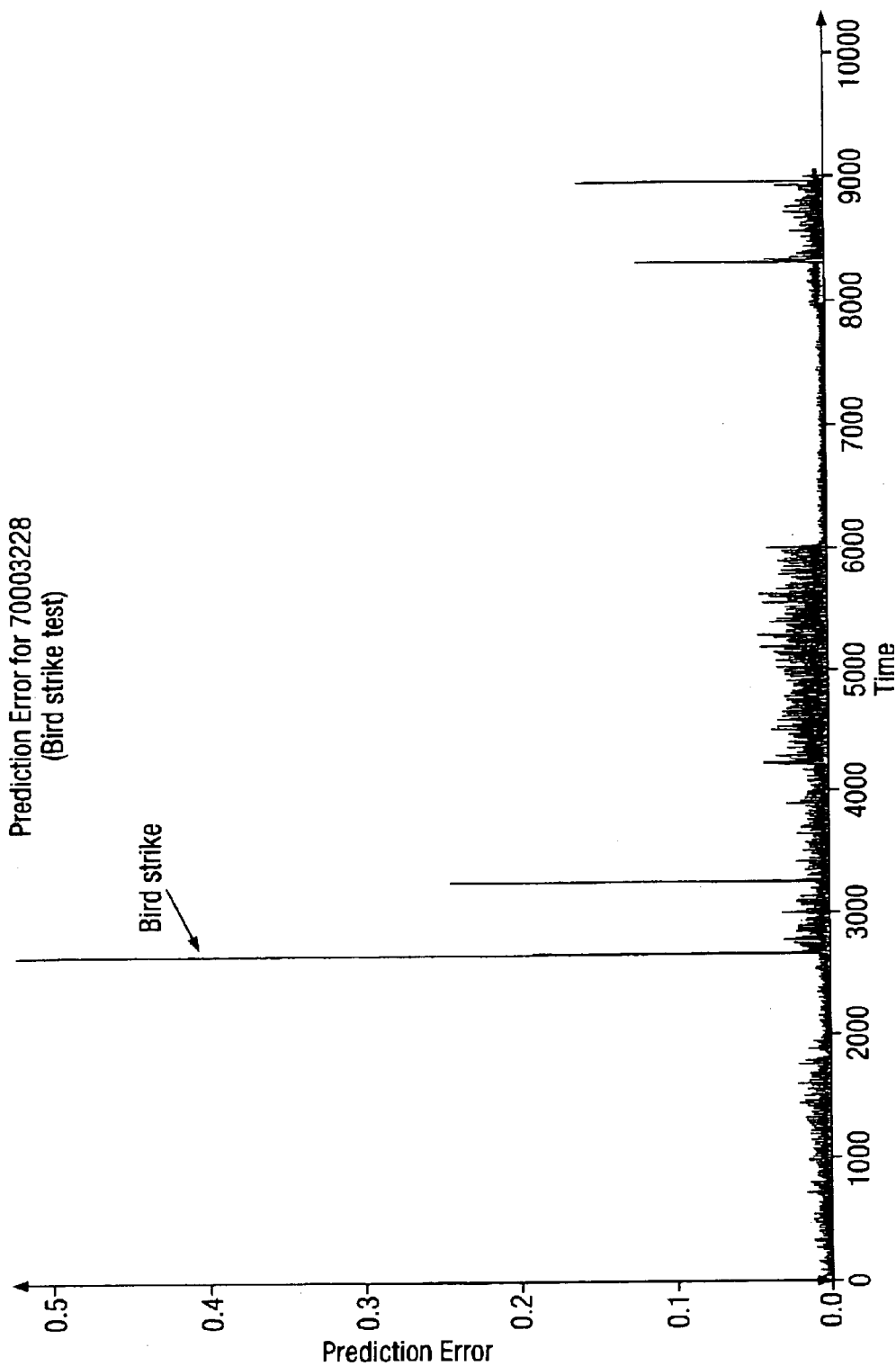
FIG. 4 shows a graph of the prediction error for the learnt model for a further engine operating period in which the engine experienced a bird strike.

FIG. 4 shows a graph of the prediction error for a further engine operating period. In this case, however, the engine experienced a bird strike. The largest peak in the graph corresponds to the moment of bird impact. Clearly the model was able to recognise this event. However, the changed prediction error signal (compared to the baseline of FIG. 3) after the event showed that the model was also able to detect post-impact abnormal engine behaviour. This provides confidence that the model can not only detect major events such as bird strikes, but also more subtle deviations from normality.

The second method employs a process model which has a state vector associated with it (see below). The observation vector (i.e. the condition signature) has elements corresponding to measured values of performance parameters and vibration information so that two types of data are fused within the model. The fusion of the data is performed in real-time with a new output being generated by the system several times a second.

An important aspect of the use of this model in the system is the use of learning. In a first, off-line, phase of learning, a generic model of the engine is learnt. The learning is data-driven using an algorithm such as Expectation-Maximisation in order to maximise the likelihood of the learnt model given the training data. Once such a generic model has been learnt off-line for a particular type of engine, learning can then be applied on-line in order to tune the model to an individual engine immediately after its pass-off test and after each maintenance procedure. Engine deterioration can also be learnt on-line. The learnt model can be tuned to different flight conditions, such as cruising or landing, in order to detect novelty with even more sensitivity and specificity.

The data-driven learnt model may be integrated with existing performance models which rely on the laws of thermodynamics and computational fluid dynamics (knowledge-based models). Such models can therefore be described as hybrid models because they are based on the integration of learnt and knowledge-based models.

Looking in more detail at the learnt modelling approach, it is based on the application of Expectation Maximisation (EM) to parameter estimation in linear dynamical systems (see Ghahramani and Hinton, *Parameter Estimation for Linear Dynamical Systems*, Technical Report CRG-TR-96-2, University of Toronto, 1996) and to non-linear systems (see Roweis and Ghahramani, "A Unifying Review of Linear Gaussian Models", *Neural Computation*, 11, 305–345, 1999; and Ghahramani and Roweis, "Learning in Nonlinear Dynamical Systems Using an EM Algorithm" in Kearns et al. (editors), *Advances in Neural Information Processing Systems*, Volume 11, MIT Press, 1999).

The EM learning algorithm is applied to a Kalman filter model. In the linear case, this is a system with a measurement process of the form $$y(i)=Cx(i)+v(i) \qquad (1)$$

where y(i) is a set of observations of hidden state x(i), C is a covariance matrix, and measurement noise v(i) is zero-mean and normally distributed with covariance matrix R. y(i) and x(i) can be the same dimension. Non-zero off-diagonal terms in C allow the model to account for inter-dependencies between the performance parameter and vibration measurements of the condition and normal signatures. The state equation is $$x(i+1)=Ax(i)+w(i) \qquad (2)$$

with w(i) zero-mean and normally distributed with covariance matrix Q.

At the beginning of the training phase A and C are initialised to small random values (e.g. with elements of the matrices $\approx 10^{-5}$), and R and Q are initialised e.g. to I. Then during the training phase, for each condition signature y(i) in the training set, the method of Roweis and Ghahramani applied to equation (2) to derive the most likely values for the elements of x(i), and the elements of C, R and v(i) are iteratively adjusted so that Cx(i)+v(i) converges to the respective condition signature (R and Q can be constrained throughout to be diagonal matrices). Convergence can be determined by the log-likelihood of the set of observations given the model.

Instead of initialising the elements of A to small random values, it is also possible to adopt initial values that embody existing performance models of engine behaviour. After the training phase, the model would then be a hybrid of a knowledge-based and a data-driven model. By fusing these two methods of data-analysis, the accuracy of prior expert knowledge can be combined with the robustness of data-driven approaches.

When the training phase has ended and the model is receiving real-time data consisting of a sequence of condition signatures, the Kalman filter is again used to derive the most likely values for the elements of x(i) for each condition signature y(i). However, the elements of C and v(i) are now fixed, so Cx(i)+v(i) provides the normal signature for comparison with the condition signature.

For example, comparison of the normal signature with the condition signature can be on the basis of the normalised innovations squared (NIS). The innovations sequence v is the difference between the condition signature and the normal signature, so $$v(k)=y(k)-C\hat{x}(k|k-1) \quad (3)$$

The innovations should be zero-mean and white.

The NIS combines the individual innovations sequences.

$$NIS(k)=v^T(k)S(k)^{-1}v(k) \quad (4)$$

The individual sequences are weighted by the term $S(k)^{-1}$, the inverse of the innovation covariance given by $$S(k)=C(k)P(k|k-1)C(k)^T+R(k) \quad (5)$$

where P(k|k−1) is the prediction covariance.

The model is first illustrated by a simple example (which does not use vibration measurements) where observations are made of the speeds of the three shafts of a test engine during cruise. The observed data y is simply the state x corrupted by noise, so $$y(i)=x(i)+v(i) \quad (6)$$

The observations are used during the learning process, to generate a dynamical system model in which A, C, Q and R are learned from the data. At the beginning of the training phase A and C were initialised to small random values and R and Q were initialised to I.

Figure 5:
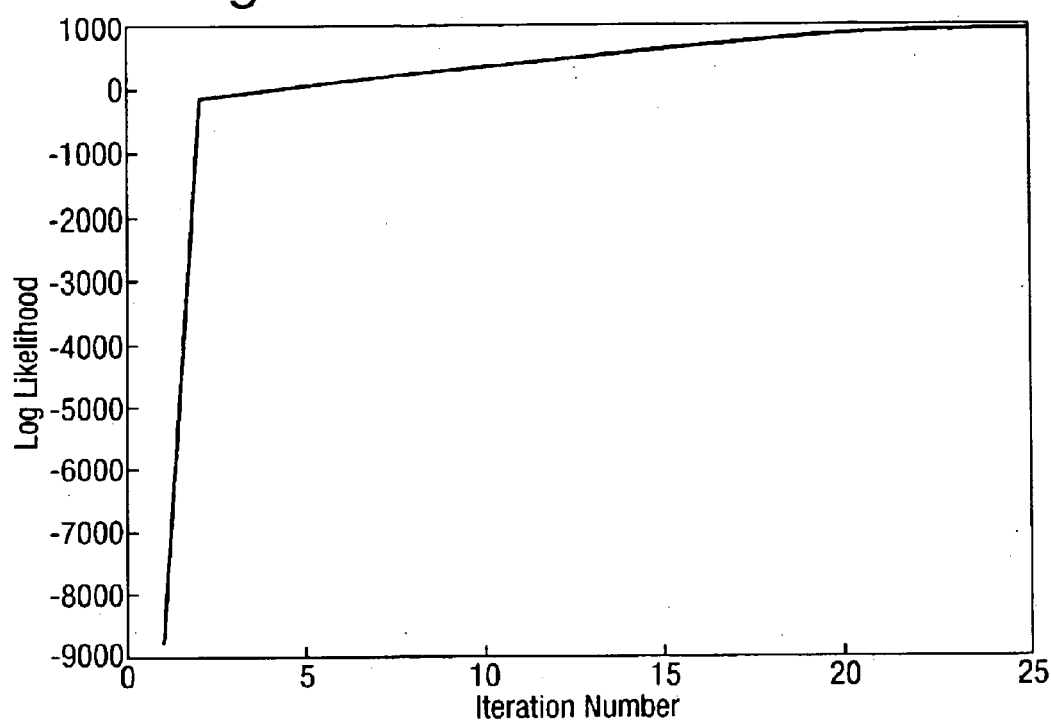
FIG. 5 shows the learning curve for a simple example of a system model for operation of the first aspect of the invention.
Figure 6:
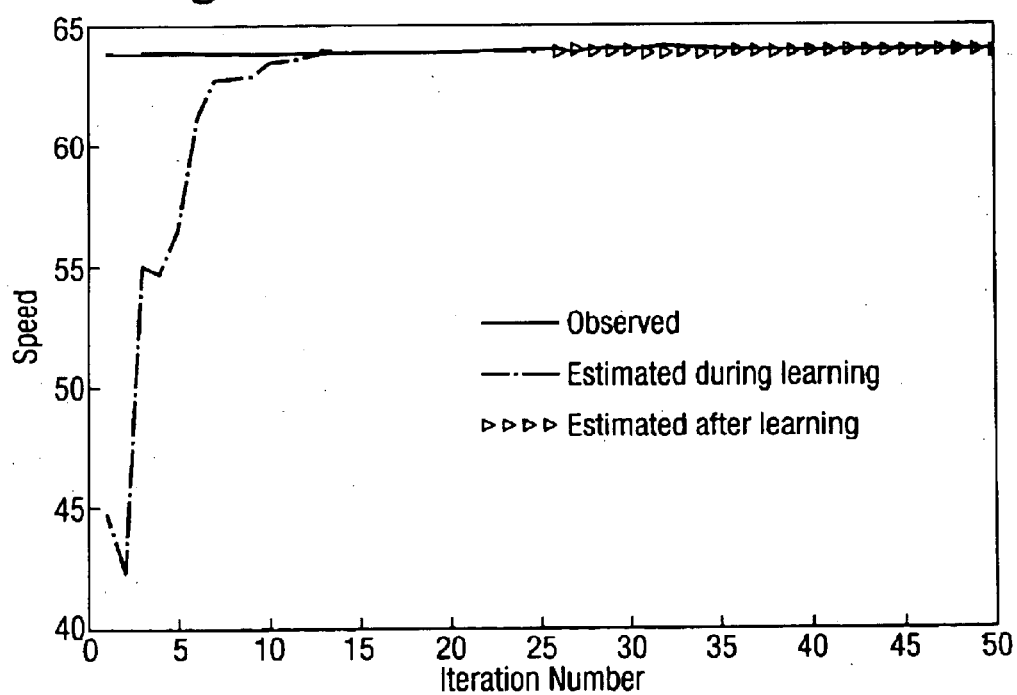
FIG. 6 shows a comparison of observations and modelled estimates for a shaft speed measurement, illustrating evolution of the model of FIG. 5.

FIG. 5 illustrates the learning (log likelihood) plot for the system. FIG. 6 shows the evolution of estimates of shaft 1 speeds during the learning process using the EM algorithm. In the example shown, the learning stage lasts for the first 25 iterations. From iteration 25 onwards, the system's dynamical properties are determined by the learned matrices (which are then kept fixed).

Once trained, the systems can be used to detect events or abnormalities, that is to say divergences from the learnt model of normality. The events of particular interest are those that are unexpected, possibly indicating a problem with the engine for example. However, particularly where the models have been learned only for "steady state" parts of the flight envelope (e.g. acceleration, cruise and deceleration), transients during operation of the engine will also be flagged up as events, although they are expected. For example, where a bleed valve is opened or closed, the operating condition of the engine will exhibit significant differences from a learnt model of steady state normality which does not include this event.

Thus when using such a steady state model, measures can be employed to avoid these transient events. For instance, since the opening of a bleed valve is an event that occurs at a defined point in time, the data collected from the engine at that time and slightly either side of it (e.g. for 2 seconds before and after) can be eliminated from the data analysed by the health monitoring system.

The approach is next illustrated with a more elaborate example which uses both performance parameter and vibration data. In this example the model was applied to data acquired from a test bed-mounted, multi-shaft, aero gas turbine engine which was undergoing a cyclic acceleration-deceleration test when it experienced an intermediate pressure turbine lock-plate event. Such tests are used to investigate engine behaviour under extreme conditions. The data was acquired synchronously as described above.

A lock-plate event occurred in the engine on test day 152-00. The training data was 152-00 data for a period before the event, and the test data was 152-00 data for the period including the event. In this example a 14 dimensional model (i.e. y(i) and x(i) each had 14 elements) was used in which the condition indicator inputs were:

The tracked orders of the low pressure (tol), intermediate pressure (toi) and high pressure (toh) shafts, The shaft speeds of the low pressure (N1V), intermediate pressure (N2V) and high pressure (N3V) shafts, The ambient (P0V), total inlet (P20V), high pressure compressor delivery (P30V) and exhaust (PEXV) pressures The total inlet (T20V) and high pressure compressor delivery (T30V) temperatures, The turbine gas temperature trimmed (TGTTRM)

The demanded fuel flow (WFDEM)

At the beginning of the training phase A and C were initialised to small random values and R and Q were initialised to I.

FIG. 7 shows the measured low pressure shaft speed (N1V) for part of the period of the test data, and FIG. 8 shows the value for the NIS calculated by the trained model over the same period.

The first two sharp troughs in the N1V trace were caused by planned consecutive cyclic decelerations. Associated with each of these troughs are two NIS peaks. These peaks indicated that the engine was not behaving normally during the cyclic testing. In fact subsequent examination revealed that a lock plate had released earlier during the test and as a result abnormal blade rubbing was occurring during each of the deceleration cycles.

During the third planned deceleration cycle in the period covered by FIGS. 7 and 8 (i.e. at approximately data point 12850) the engine sustained blade damage which resulted in the sharp NIS peak and drop off in N1V.

However, the earlier (all be it smaller) NIS peaks demonstrate that the monitoring system was able to detect the effect of the lock plate release in real time and before substantial blade damage was sustained. If such a release had occurred in an in-service aero engine, it would therefore have been possible to generate an immediate warning so that timely action (such as engine inspection or maintenance) could have been performed. In contrast, sudden variations in N1V can occur normally, so N1V alone is not a reliable indicator of abnormal behaviour.

A further example also uses both performance parameter and vibration data. Again the model was applied to synchronously data acquired from a test bed-mounted, multi-shaft, aero gas turbine engine. However, in this case an oil seal leak developed in the engine.

The fault occurred in the engine around data point 50410. The training data was from a period before the fault, and the test data was for a period including the fault. In this example a 13 dimensional model was used in which the condition indicator inputs were tol, toi, toh, N1V, N2V, N3V, P0V, P20V, P30V, PEXV, T20V, TGTTRM, and WFDEM.

Figure 9:
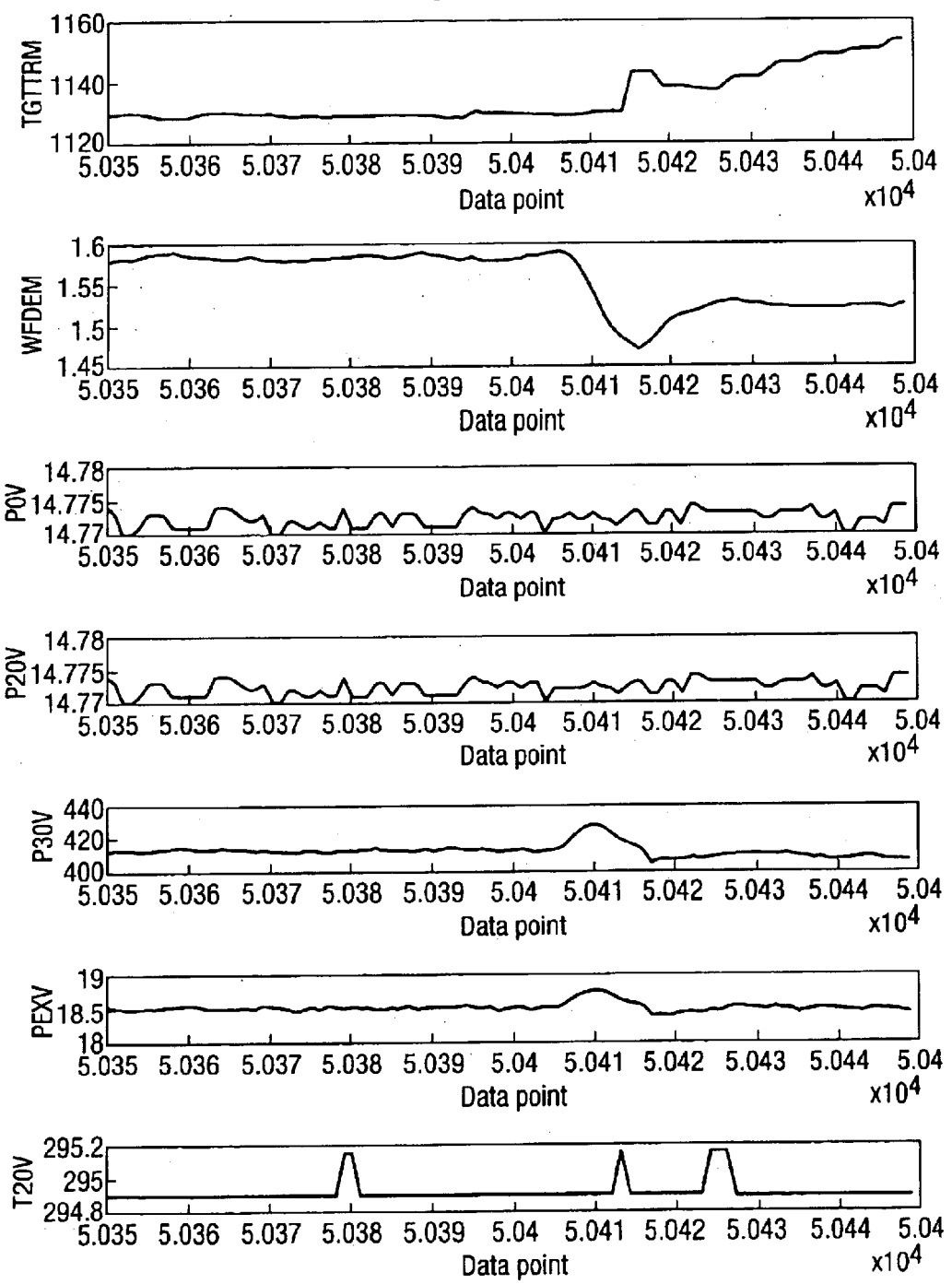
FIG. 9 shows the values for the 13 condition indicators and the NIS over the same period from a further example of the system model.
Figure 9:
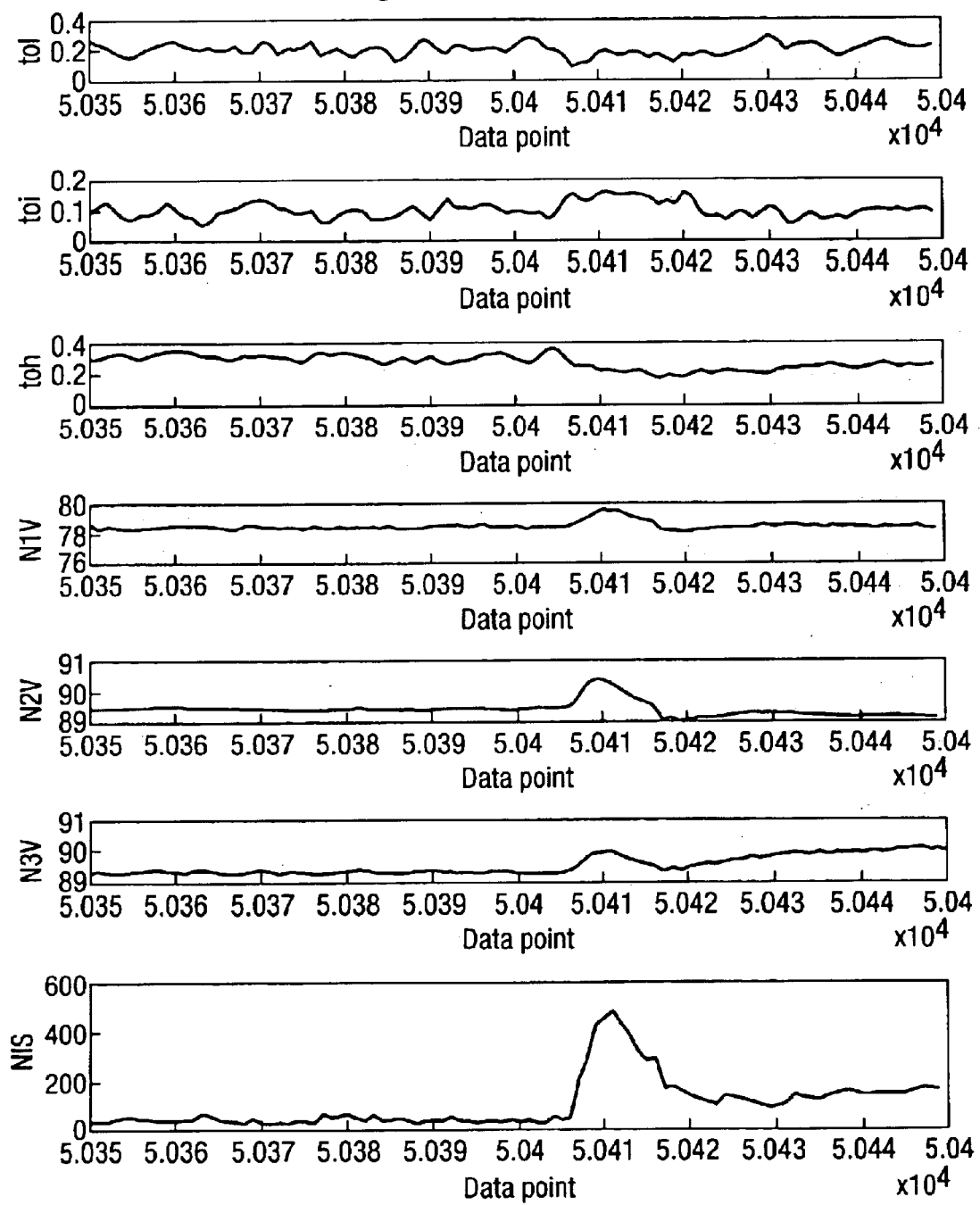

FIG. 9 shows the values for the 13 condition indicators and the NIS (in the bottom graph) over the period including the event. The sharp NIS peak at data point 50410 again demonstrates that the monitoring system was able to detect the moment of the event. Although some of the other condition indicators also had peaks at this time, by themselves they cannot be reliably associated with abnormal (novel) behaviour.

Subsequent examination showed that the event was an oil seal leak which allowed engine oil to enter the combustor. Because of this leak the engine control system reduced the amount of fuel entering the combustor (hence the drop in WFDEM) to maintain the engine thrust (given by PEXV/P20) at a constant level.

After the event, with oil continuing to leak into the combustor, the engine was operating outside the scope of normal behaviour. This was successfully picked up by the NIS trace which after data point 50410 did not return to its pre-event level.

Next we consider how a health monitoring system, incorporating the model described above, could be installed for in-flight analysis of aero gas turbines.

Figure 10:
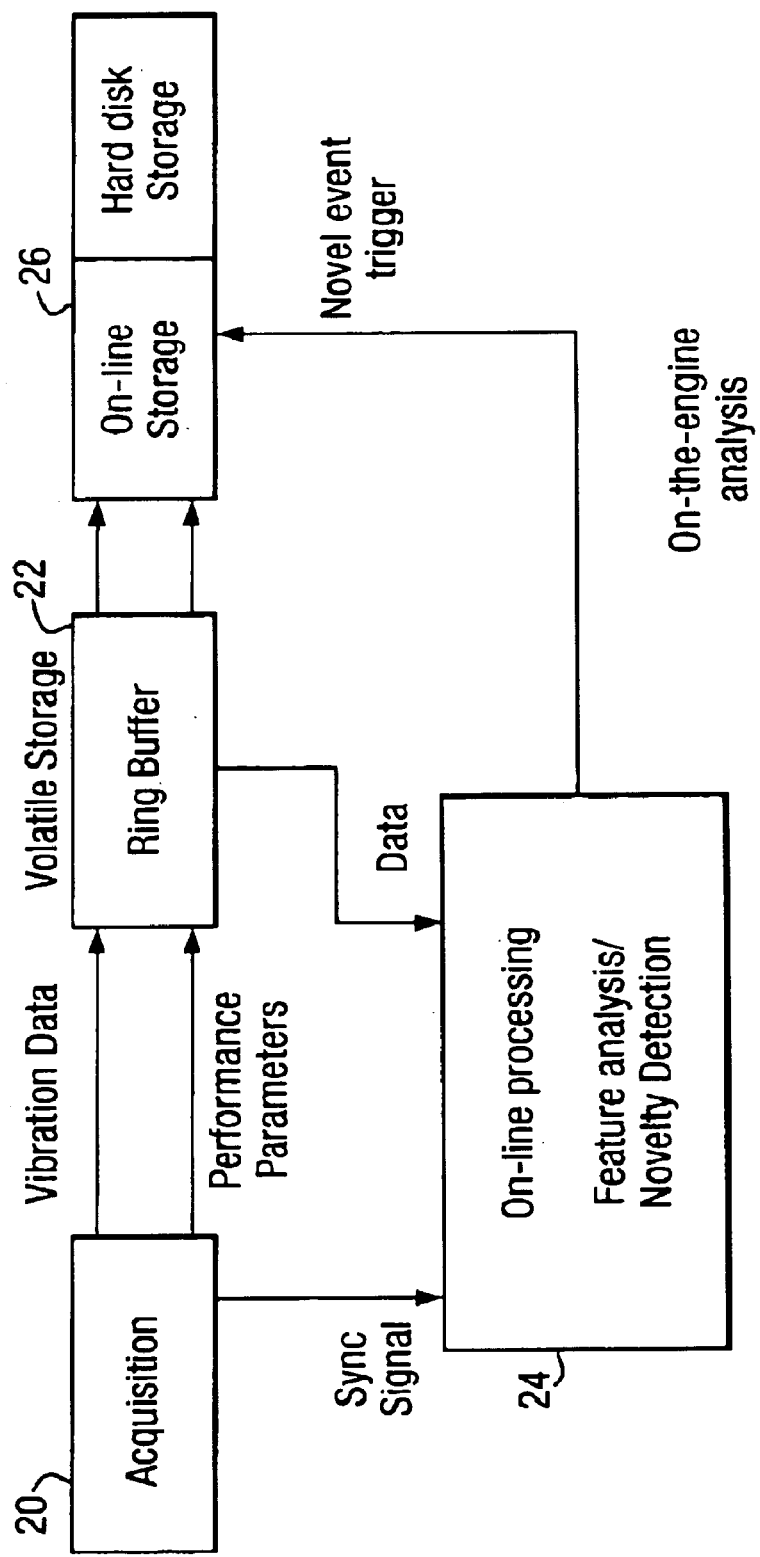
FIG. 10 shows a schematic example of an on-the-engine health monitoring system.

An on-the-engine system, shown schematically in FIG. 10, could generate of the order of 1 Gb of vibration and performance data (consisting mainly of pressures, temperatures and shaft speeds) per flight. The vibration data is usually analysed in the frequency domain. The vibration and performance data, as they are being generated by data acquisition means 20, are temporarily stored in ring buffer 22. The data is synchronised and subjected to novelty detection in processor and comparator means 24 which receives a synchronisation signal from data acquisition means 20 and the data from ring buffer 22. Those sections of the data corresponding to novel events are then tagged and recorded with no loss of information (i.e. highbandwidth data is recorded) in registration means 26 which has semi-permanent on-line and/or hard disk storage. When the flight is completed the stored data may be downloaded and subjected to more intensive ground-based analysis.

The system may also include a display which is driven to allow information to be displayed either during acquisition or for review once an acquisition cycle has been completed. It preferably includes the following features:

Ability to display the result of the comparison of the condition signature with the normal signature, e.g. in the form of the NIS or the prediction error. An unhealthy event may be highlighted e.g. with an alert signal Ability to display a combination of any two of vibration spectra, tracked orders, broadband power, performance parameters synchronised in time.

Ability to extract and plot vibration spectra against engine speed.

Ability to interrogate and print any of vibration spectra, tracked orders, broadband power and performance parameters.

Automatic detection and display of features from vibration spectra (sidebands, harmonics, etc.)

While the invention has been described in conjunction with the examples described above, many equivalent modifications and variations will be apparent to those skilled in the art when given this disclosure. Accordingly, the examples of the invention set forth above are considered to be illustrative and not limiting. Various changes to the described examples may be made without departing from the spirit and scope of the invention.

All the references mentioned above are hereby incorporated by reference.

We claim:

1. A method for monitoring the health of a system, which comprises performing at each of a plurality of times the steps of:
   constructing a condition signature for a present time from a plurality of condition indicators including (a) a plurality of vibration measurements acquired from said system or (b) one or more vibration measurements and one or more performance parameter measurements acquired from said system;
   predicting a normal signature from a model defining one or more inter-dependencies between condition indicators used to construct the condition signature for a previous time, said normal signature corresponding to a condition signature for a healthy system at the present time, and said model comprising a matrix with one or more non-zero off-diagonal terms to define said inter-dependencies;
   comparing said condition signature for the present time with said normal signature; and
   registering an event if said condition signature for the present time differs from said normal signature by more than a predetermined threshold.

2. A method according to claim 1, wherein said model is a learned model.

3. A method according to claim 1, wherein the step of comparing said condition signature with said normal signature involves calculating a value for the normalised innovations squared.

4. A method according to claim 1, wherein said model comprises a neural network.

5. A method according to claim 4, wherein the step of comparing said condition signature with said normal signature involves calculating a prediction error.

6. A method according to claim 1, wherein said times define successive intervals of at most 1 sec duration.

7. A method for monitoring the health of a system, which comprises performing at each of a plurality of times defining successive intervals of at most 1 sec duration the steps of:
   constructing a condition signature for a present time from a plurality of condition indicators including (a) a plurality of vibration measurements acquired from the system or (b) one or more vibration measurements and one or more performance parameter measurements acquired from said system, said measurements being synchronously acquired from said system to a synchronization imprecision of at most 1 sec;
   predicting, from condition indicators used to construct the condition signature for a previous time, a normal signature corresponding to a condition signature for a healthy system at the present time;

comparing said condition signature for the present time with said normal signature; and registering an event if said condition signature for the present time differs from said normal signature by more than a predetermined threshold.

8. A method according to claim 7, wherein said normal signature is predicted from a model defining one or more inter-dependencies between said condition indicators used to construct the condition signature for the previous time.

9. A method according to claim 8, wherein said model is a learned model.

10. A method according to claim 8, wherein said model comprises a matrix with one or more non-zero off-diagonal terms to define said interdependencies.

11. A method according to claim 10, wherein the step of comparing said condition signature with said normal signature involves calculating a value for the normalised innovations squared.

12. A method according to claim 8, wherein said model comprises a neural network.

13. A method according to claim 12, wherein the step of comparing said condition signature with said normal signature involves calculating a prediction error.

14. A method according to any one of claim 1, wherein said measurements are synchronously acquired from said system to a synchronisation imprecision of at most 1 sec.

15. A method according to any one of claims 1, wherein said system comprises a gas turbine engine.

16. A data processing system for monitoring the health of a system, comprising:

data acquisition means for acquiring a plurality of condition indicators from said system at each of a plurality of times, said condition indicators including (a) a plurality of vibration measurements or (b) one or more vibration measurements and one or more performance parameter measurements;

processor means for constructing a condition signature for a present time from said condition indicators and for predicting a normal signature corresponding to a condition signature for a healthy system at the present time, said normal signature being predicted by a model which defines one or more inter-dependencies between condition indicators used to construct the condition signature for a previous time, wherein said model comprises a matrix with one or more non-zero off-diagonal terms to define said inter-dependencies;

comparator means for comparing said condition signature for the present time with said normal signature; and registration means for registering an event if said comparator for the present time indicates that said condition signature differs from said normal signature by more than a predetermined threshold.

17. A data processing system for monitoring the health of a system, comprising:

data acquisition means for acquiring a plurality of condition indicators from said system at each of a plurality of times defining successive intervals of at most 1 sec duration, said measurements being synchronously acquired from said system to a synchronization imprecision of at most 1 sec, and said condition indicators including (a) a plurality of vibration measurements or (b) one or more vibration measurements and one or more performance parameter measurements;

processor means for constructing a condition signature for a present time from said condition indicators and for predicting, from condition indicators used to construct the condition signature for a previous time, a normal signature corresponding to a condition signature for a healthy system at the present time;

comparator means for comparing said condition signature for the present time with said normal signature; and registration means for registering an event if said comparator for the present time indicates that said condition signature differs from said normal signature by more than a predetermined threshold.

18. A method for monitoring the health of a system, which comprises performing at each of a plurality of times the steps of:

constructing a condition signature for the present time from a plurality of condition indicators including (a) a plurality of vibration measurements acquired from said system or (b) one or more vibration measurements and one or more performance parameter measurements acquired from said system, said measurements being synchronously acquired from said system to be a synchronization imprecision of at most 1 sec;

predicting a normal signature from a model defining one or more inter-dependencies between condition indicators used to construct the condition signature for the previous time, said normal signature corresponding to a condition signature for a healthy system at the present time;

comparing said condition signature for the present time with said normal signature; and registering an event if said condition signature for the present time differs from said normal signature by more than a predetermined threshold.

19. A data processing system for monitoring the health of a system, comprising:

data acquisition means for synchronously acquiring a plurality of condition indicators from said system at each of a plurality of times to a synchronization imprecision of at most 1 sec, said condition indicators including (a) a plurality of vibration measurements or (b) one or more vibration measurements and one or more performance parameter measurements;

processor means for constructing a condition signature for the present time from said condition indicators and for predicting a normal signature corresponding to a condition signature for a healthy system at the present time, said normal signature being predicted by a model which defines one or more inter-dependencies between condition indicators used to construct the condition signature for the present time;

comparator means for comparing said condition signature for the present time with said normal signature; and registration means for registering an event if said comparator for the present time indicates that said condition signature differs from said normal signature by more than a predetermined threshold.

* * * * *